United States Patent [19]

Murao et al.

[11] 4,382,888
[45] May 10, 1983

[54] TRYPTOPHAN DERIVATIVE AND PROCESS FOR PRODUCTION THEREOF

[75] Inventors: Sawao Murao, Sakai; Kenichi Fukuhara, Yokohama, both of Japan

[73] Assignee: Ajinomoto Company Incorporated, Tokyo, Japan

[21] Appl. No.: 201,389

[22] PCT Filed: Nov. 15, 1979

[86] PCT No.: PCT/JP79/00295
§ 371 Date: Jul. 14, 1980
§ 102(e) Date: Jul. 14, 1980

[87] PCT Pub. No.: WO80/01069
PCT Pub. Date: May 29, 1980

[30] Foreign Application Priority Data
Nov. 17, 1978 [JP] Japan ............................ 53-142081

[51] Int. Cl.$^3$ ..................... C07C 103/52; C12P 21/02; C12N 1/20

[52] U.S. Cl. ............................... 260/112.5 R; 435/70; 435/253

[58] Field of Search ................... 260/112.5 R; 435/70, 435/253

[56] References Cited
PUBLICATIONS

Chem. Abstr. vol. 93, 1980, 219326q.

*Primary Examiner*—Delbert R. Phillips
*Attorney, Agent, or Firm*—Oblon, Fisher, Spivak, McClelland & Maier

[57] ABSTRACT

N-(6-Deoxy-L-talosyloxyhydroxyphosphenyl)-L-leucyl-L-tryptophan which is novel compound having an inhibitory activity against a metallo proteinases produced by *Pseudomonas aeruginosa*, and a process for biochemically producing the compound according to the genus Streptomyces.

1 Claim, 1 Drawing Figure

TRYPTOPHAN DERIVATIVE AND PROCESS FOR PRODUCTION THEREOF

FIELD OF THE ART

The present invention relates to a novel tryptophan derivative having an inhibitory activity against metallo proteinases, and a process for biochemically producing the tryptophan derivative. The novel metallo proteinase inhibitor is useful for medicine such as an agent for treating *Pseudomonas aeruginosa* infections disease and an agent for regulating growth of a microorganism. The microorganism for producing such derivative is *Streptomyces mozunensis*, which is a new species of the genus Streptomyces.

BACKGROUND OF THE ART

Proteinase inhibitors are useful in a medical field, and some of them are put to practical use. Particularly, it is thought that a metallo proteinase inhibitor can be used as an agent for treating *Pseudomonas aeruginosa* infectious disease. It is known that the metallo proteinase of *Pseudomonas aeruginosa* plays an important part for *Pseudomonas aeruginosa* infectious disease.

On the other hand, in a field of biochemistry, the material having inhibitory activity against a metallo proteinase produced by a microorganism, is useful. For example, it is expected that the material is used for regulating growth and metabolism of a microorganism.

Accordingly, it is significant in a field of medicine and biochemistry that a material inhibiting against the metallo proteinase produced by *Pseudomonas aeruginosa* is given.

Phosphoramidon (*The Journal of Antibiotics* 26, [10], 621 (1973) and S-MPI (*Agric. Biol. Chem.*, 42, [4],899 (1978)) are known as a metallo proteinase inhibitor produced by the genus Streptomyces, and differ from the object compound of the present invention.

DISCLOSURE OF THE INVENTION

The present invention relates to a novel compound, N-(6-deoxy-L-talosyloxy hydroxyphosphinyl)-L-leucyl-L-tryptophan having the following structural formula:

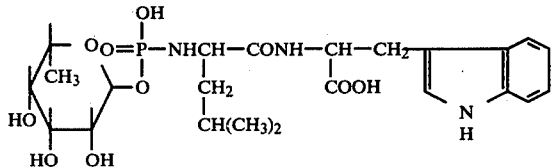

which hereinafter may be referred to as novel tryptophan derivative, and to a process for producing the novel tryptophan derivative which comprises culturing a microorganism belonging to the genus Streptomyces and capable of producing novel tryptophan derivative, which may be referred to as novel tryptophan derivative producing microorganism, producng the novel tryptophan derivative in the culture medium and recovering it.

The novel tryptophan derivative may be in the salt form and ester form. The hydroxyl group in the sugar moiety of the compound may be protected. The salt and ester thereof, wherein phosphoric acid residue and/or carboxyl group are modified, is within the present invention. Examples of the salt are metal salts such as sodium, potassium, rubidium, cesium, and calcium salt, and ammonium salt. Examples of the ester are alkyl, aryl and aralkyl ester such as methyl, ethyl, phenyl and benzyl ester.

As protecting group for hydroxyl group of the sugar moiety, one in common use as protecting group for hydroxyl group of the part of sugar mentioned above, for example, acyl group such as acetyl and benzoyl group can be used.

Novel tryptophan derivative can be produced by culturing novel tryptophan derivative producing microorganism and recovering the tryptophan derivative produced in the culture medium.

As liquid medium used in a culture of the microorganism, one in common use for culturing ordinary microorganism may be able to be used.

Carbon source which can be assimilated by novel tryptophan derivative producing microorganism, for example, carbohydrates such as glucose, galactose, maltose, starch and hydrolyzed starch, alcohol such as glycerol, nitrogen source, for example, ammonium salts such as ammonium sulfate and ammonium chloride, amino acids, peptone, meat extract, hydrolyzed soy bean, and inorganic salts, and materials containing minor nutrients, if necessary, may be used.

The microorganism may be cultured, for example, usually at pH 5.0 to 9.0, and at a temperature of 15° to 40° C. under aerobical condition such as shaking and airation with stirring.

The novel tryptophan derivative is produced in the culture medium of the novel tryptophan derivative producing microorganism and in the microorganism. It is produced mostly in the medium. The novel tryptophan derivative is isolated from the cultured medium of the microorganism, by a combination of appropriated methods of separation and purification, such as extraction with butanol, dialysis, adsorption by adsorbent such as activated carbon, and chromatographies such as ion exchange, adsorption, partition and gel filtration chromatography.

Example for production of the novel tryptophan derivative is as follows:

A medium containing peptone, meat extract and sodium chloride in a ratio of 10 grams of peptone, 10 grams of meat extract and 3 grams of sodium chloride per 1 l of water, was adjusted to pH 7.0. Each 40 ml of such medium was poured into ten 500 ml-Sakaguchi-flasks, respectively.

The flasks were heated for sterilization at 120° C. for 10 minutes.

Each one loopful inoculum of *Streptomyces mozunensis* AJ 9406 FERM-P 4589, NRRL 12054 was transferred from slant culture to the culture medium. The medium was shaken at 30° C. for 24 hours (120 times/minute).

400 ml of the cultured medium obtained above was transferred to 20 l-jar-fermentor made of stainless steel containing 15 l of sterilized medium, which is adjusted to pH 7.0, having a composition of glycerol 10 g, peptone 40 g, potassium phosphate ($K_2HPO_4$) 1 g sodium chloride 1 g, magnesium sulfate 7 hydrate 0.5 g, ferrous sulfate 7 hydrate 0.01 g, cupric sulfate 5 hydrate 1 mg, Zinc sulfate 7 hydrate 1 mg, and manganese sulfate 6 hydrate 1 mg per 1 l of water. The obtained mixture was stirred (300 rpm) for main fermentation at 30° C. with sterilized air (20 l/minute). After 23 hours' fermentation, microorganism was removed by centrifugation from culture medium (pH value: about 8.5) and thereby supernatant liquid (14 l) was obtained. The inhibitory activity of 50 μl of such supernatant against the metallo proteinase of *Pseudomonas aeruginosa* was 50% according to method of measuring inhibition ratio of enzyme activity mentioned after.

To this supernatant (14 l) activated carbon (produced by Wako Pure Chemical Industries Co., Inc.) (700 g) was added and the obtained mixture was stirred for 30 minutes. Carbon was separated by filtration and washed with 3 l of pure water 3 times, and then washed with 15 l of 90% methanol containing ammonia (0.1N solution). Thus obtained washings were mixed and concentrated under reduced pressure to 400 ml of volume. Thus concentrated solution was adjusted to pH 2 at 4° by adding 3 normal hydrochloric acid. Organic material was extracted with n-butanol (400 ml). Thus obtained butanol layer was adjusted to pH 7 at 4° C. by adding 3 normal sodium hydroxide and the butanolic mixture was extracted with water (400 ml). The aqueous layer was evaporated to dryness under vacuum and the residue was dissolved in 200 ml of 1 normal acetic acid.

Thus obtained solution was applied to a column (4.5 cm×25 cm) of DEAE-Sephadex A-25 (produced by Pharmacia Co., Inc.) which had been washed enough with 1 normal acetic acid at 4° C., and then the column was washed with 2.8 l of 1 normal acetic acid. Linear gradient elution from 4 l of 1 normal acetic acid to 4 l of 1 normal acetic acid containing sodium chloride (0.5 M) was carried out. Thus fractionated eluent was collected by fraction collector and thereby fractions having inhibitory activity against the metallo proteinase of *Pseudomonas aeruginosa* was collected.

Such collected fractions were mixed and poured into column (3.5 cm×15 cm) of activated carbon for chromatography (produced by Wako Pure Chem. Inc. Co., Inc.) which had been washed enough with conc. hydrochloric acid, methanol, and water successively. The column was washed enough with water until eluent from the column showed negative silver nitrate-reaction. An elution with 85% methanol containing ammonia (pH 10.5) was carried out.

The fractions containing the desired product was combined, concentrated to 3 ml of volume under vacuum, and applied to a column (2.5 cm×40 cm) of Sephadex G-10 (produced by Pharmacia Co., Inc.) which had been previously washed enough with water. The elution with 200 ml of water was carried out. The desired product was eluted in a first about 135 ml eluate. The fraction containing the desired product was freeze-dried to give white powder (500 mg).

Thus obtained white powder has following properties, and therefrom it was determined as N-(6-deoxy-L-talosyl-oxyhydroxyphosphinyl)-L-leucyl-L-tryptophan.

1. Elemental Analysis (di-cyclohexylammonium salt): Found C56.60%, H8.21%, N9.31%; Calcd. for $C_{23}H_{34}N_3O_{10}P \cdot (C_6H_{13}N)_2$ C56.67%, H8.15%, N9.44%.

2. Molecular Weight (Method according to Mass Spectrometry): 543

3. Melting point (di-cyclohexylammonium salt): 153~156° C. (dec.)

4. Specific Rotation: $[\alpha]_D^{21} = -25.6°$ (di-cyclohexyl ammonium salt: C=0.5, $H_2O$)

5. IR (KBr) Spectra: FIG. 1, $\nu_{max}$ ($cm^{-1}$): 3400~3100 (OH, NH), 2950 (CH)~1640 (Amide I), 1590 (Phenyl), 1520 (Amide II), 1400 (CH), 1200 P=O), ~1070 (C—O), 740 (Phenyl)

6. Colour Reaction: Positive to Rydon-Smith, Ehrlich, diphenylamine-aniline and molibdate-perchloric acid reagents; negative to ninhydrin reagent.

7. Constituting Amino Acid: Leucine and Truptophan (The material hydrolyzed with 6 normal hydrochloric acid or 4 normal sodium hydroxide were analyzed according to Automatic Amino Acid Analizer for determination of Amino Acid.)

8. Constituting Sugar: 6-deoxy-L-talose (Experiment: A sample was stood overnight in 0.5 normal hydrochloric acid at room temperature for hydrolysis. The solution obtained by hydrolysis was successively passed through a column packed with active carbon for chromatography (produced by Pure Chem. Ind. Co., Inc.), Dowex 50 [H+], produced by Dow Chemical Co., Inc.), and Anbirlite IRA-402 [OH−] (produced by Rohm & Haas Co., Inc.). The eluate was concentrated under reduced pressure to isolate a sugar. The sugar was identified as 6-deoxy-L-talose, from value of specific rotation, thin layer chromatography, gas chromatography and high performance liquid chromatography.)

9. Thin Layer Chromatography: ①$R_f$=0.41 (single spot, thin layer plate of Kieselgel 60 produced by E. Merck Co., Inc.; Developing solvent, n-butanol-acetic acid-water (4:1:1), Color-producing reagent: 10% sulfuric acid) ②$R_f$=0.49 (single spot; developping solvent, n-butanol-pyridine-acetic acid-water (15:10:13:12); other conditions, mentioned above.)

10. UV Spectra: $\lambda_{max}^{H2O}$ ($\epsilon$)~280 (5,700)

11. NMR Spectra:

(1) 'H-NMR (90 MHz, in $D_2O$) was shown in Table 1. Internal Standard: 3-(trimethylsilyl)-propan sulfonic acid sodium salt (2) $^{13}$C-NMR (25.2 MHz, in $D_2O$) was shown in Table 2.

Internal Standard: Dioxane

Chemical Shift; lower magnetic field than that of dioxan: +, higher magnetic field than that of dioxan: −

TABLE 1

| Chemical Shift (δ) | Number of Proton, Assignment of Signals |
|---|---|
| 0.8 ppm | 6H, hydrogen in δ, δ' position of leucine |
| 1.2 ppm | 3H, α, J=6.5 Hz, hydrogen of methyl group in sugar |
| 1.0~1.7 ppm | 3H, m hydrogen in β, γ position of leucine |
| 3.1~3.8 ppm | 6H, m hydrogen in 2, 3 and 4 position of sugar, hydrogen in β position of tryptophan, hydrogen in α-position of leucine |
| 3.95 ppm | 1H, q, J=6.5 Hz, hydrogen in 5 position of Sugar |
| 4.7 ppm | 1H hydrogen in α position of tryptophan |
| 5.35 ppm | 1H, dd, Jp.CH=8 Hz, $J_{1,2}$=1 Hz, hydrogen in 1 position of sugar |
| 7.0~7.8 ppm | 5H, m, hydrogen in indole ring of tryptophan |

TABLE 2

| Chemical Shift (δ) | Assignment of Signal |
|---|---|
| 111.2 ppm | ⎫ Carbonyl carbon in tryptophan and leucine |
| 110.2 | ⎭ |
| 69.3 | ⎫ |
| 60.8 | ⎪ |
| 57.6 | ⎪ |
| 55.0 | ⎬ Carbon in indole ring of tryptophan |
| 52.4 | ⎪ |
| 52.2 | ⎪ |
| 45.1 | ⎭ |

TABLE 2-continued

| Chemical Shift (δ) | Assignment of Signal |
|---|---|
| 43.3 | |
| 29.3 | d, J=5.4 Hz (P—O—C), Carbon in 1 position of sugar |
| 5.4 | Carbon in 3 or 4 position of sugar |
| 3.7 | d, J=7.9 Hz (P—O—C—C), carbon in 2 position of sugar |
| 1.5 | Carbon in 3 or 4 position of sugar |
| −1.5 | Carbon in 5 position of sugar |
| −11.1 | } Carbon in α position of leucine or tryptophan |
| −11.9 | |
| −23.6 | d, J=5.6Hz (P—N—C—C), carbon in β position of leucine |
| −38.9 | Carbon in β position of tryptophan |
| −42.6 | Carbon in γ position of leucine |
| −44.0 | } Carbon in δ, δ' position of leucine |
| −45.6 | |
| −50.8 | Carbon in 6 position of sugar |

12. Solubility: Soluble in water, methanol and ethanol. Insoluble in benzene, hexane, ether and chloroform.

13. Colour: White

14. Action to various proteinases:

The novel tryptophan derivative has strong inhibiting activity against various metallo proteinase. Particularly, it strongly inhibits metallo proteinase produced by *Pseudomonas aeruginosa*, and thermolysin which is metallo proteinase produced by the genus Bacillus. It also inhibits metallo proteinase produced by *Aspergillus oryzae* and however does not inhibit any of pepsin, trypsin, chymotrypsin, subtilis and papain.

Amounts of the tryptophan derivative necessary for inhibiting 50% of the enzyme activity are as follows:

(1) Thermolysin: 0.35 μg p2 (2) Metallo proteinace produced by *Pseudomonas aeruginosa*: 4 μg,

[Method for measuring inhibitory activity against various proteinasis]

A mixture of 0.25 ml of sample solution in 0.05 M phosphate buffer at pH 7.5 and 0.25 ml of thermolysin solution (20 μg/ml in the same buffer was incubated for 10 minutes at 37° C. The mixture was added with 1.5 ml of 1.33% Hammarsten casein solution in 0.1M phosphate buffer (pH 7.0) and incubated for 10 minutes at 37° C. By the addition of 2 ml of 0.44 M trichloroacetic acid the reaction was stopped. After standing for 30 minutes at 37° C., the reaction mixture was filtered. To 1.0 ml of the filtrate 5 ml of 0.55 M $Na_2CO_3$ and 1 ml of 2 times diluted Folin-Ciocalteau reagent were added. After standing for 60 minutes at 37° C., the absorbance (Is) was measured at 660 mμ. The blank value (Ib) was taken by carrying out the reaction using 0.25 ml of 0.05M phosphate buffer (pH 7.5) instead of thermolysin. The control values (Es, Eb) were taken by carrying out such two reactions using 0.25 ml of 0.05 M phosphate buffer )pH 7.5) instead of the sample solution, respectively. Inhibition rate against enzyme activity is calculated by the following equation:

$$\left(1 - \frac{Is - Ib}{Es - Eb}\right) \times 100\ (\%)$$

Now, inhibitory activity against metallo proteinase produced by *Pseudomonas aeruginosa* can be measured in the same manner as above wherein amounts of enzyme used is established so as to have following value. A value of (Es−Eb) according to method for measuring inhibitory activity is 0.6 wherein cell length used for the measurement of absorbance is 1 cm.

15. Stability: Stable in weak acidic, neutral, or alkaline aqueous solution; Unstable in acidic aqueous solution (Activity is lost completely in standing for 24 hours at pH 1.)

The taxonomic criteria and methods, according to the reports of the International Streptomyces Project (ISP; E. B. Shirling and D. Gottlieb Int. J. Syst. Bacterial., 16, 313, 1966), were employed and the identification was made by the description of Bergey's Manual of Determinative Bacteriology 8th ed. ("Bergey's Manual of Determinative Bacteriology," ed. by R. E. Buchanan and N. E. Gibbons. The Williams & Wilkins Co., Baltimore, 1974), and ISP reports. The morphological, physiological and cultural properties of strain AJ-9406, FERM-P 4589, NRRL 12054 are as follows:

(a) Morphological Characteristics are as follows:

| | |
|---|---|
| Spore-bearing hyphae | Simple branching (width: 0.5~1.0μ), *Retinaculi aperti*, Spirales, and Rectiflexibiles |
| Surface structure of spores | Smooth |
| Size of spores | 0.7~1.2 × 0.9~1.6μ |
| Number of spores | 10~30 |
| Flagellated spores | Not detected |
| Globular sporangra | Not detected |
| Sporophore | Formed from aerial mycelium |
| Cell wall type | Type 1 |

(b) Cultural Characteristics

Observation of growing state in following each medium are all obedient to Method Manual, 1964 of the ISP, and the description is treated the same as example for description in the ISP.

Cultural Characteristics of Strain AJ-9406 on ISP Media after Incubation for 3 weeks at 27°~30° C. are as follows:

(1) On sucrose-nitrate agar
AM: gray, very thin powdery
VG: colorless, small colonies, scant growth
SP: none (2) On glucose-asparagine agar
AM: gray, slightly olive, powdery
VG: pale yellow, small colonies
SP: none or trace (3) On glycerine-asparagine agar (Isp. Med. No. 5)
AM: gray, powdery
VG: colorless-pale yellow, small colonies
SP: pale yellowish brown (4) On starch-inorganic salts agar (ISP Med. No. 4)
AM: gray, powder
VG: pale yellow-reddish brown, small colonies
SP: none (5) On tyrosine agar (ISP Med. No. 7)
AM: gray, powdery
VG: yellowish brown-slightly reddish brown, small colonies, slightly wrinkled
SP: light brown-reddish brown (6) On nutrient agar
AM: none
VG: pale yellow-cream, small colonies SP: none
(7) On yeast-malt extract agar (ISP Med. No. 2)
AM: gray, powdery
VG: yellowish brown, small colonies-slightly wrinkled
SP: faint brown
(8) On oatmeal agar (ISP Med. No. 3)
AM: gray, very thin powdery
VG: colorless, small colonies, very scant growth
SP: none
(9) On peptone-yeast iron agar
AM: none
VG: pale yellow-cream, small colonies
SP: none
(10) On milk
AM: none
VG: white-pale yellow, growth on surface ring
SP: none or trace
(11) On glucose-peptone gelatin stab
AM: none
VG: pale yellow-cream
SP: none AM: mass color and morphology of aerial mycelium.
VG: growth of colony and color of substrate mycelium.
SP: soluble pigment.
(c) Physiological characteristics of strain AJ-9406 are as follows:

| | |
|---|---|
| (1) Hydrolysis of starch | Positive (weak) |
| (2) Liquefaction of gelatin | Positive (slow) |
| (3) Melanoid pigment formation | |
| On peptone-yeast iron agar | Negative |
| On tyrosine agar | Negative |
| On tryptone-yeast extract broth | Negative |
| (4) Coagulation of milk | Positive |
| Peptonization of Milk | Negative |
| (5) Cell wall type | Type 1 |
| (6) Growth temperature | 15-40° C., optimum 30° C. |

| Carbon source | Utilization* |
|---|---|
| L-Arabinose | − |
| D-Xylose | − |
| D-Fructose | − |
| D-Glucose | + |
| D-Galactose | + |
| D-Mannose | − |
| L-Rhamnose | − |
| Maltose | + |
| Lactose | − |
| Sucrose | − |
| Raffinose | − |
| Inositol | − |
| D-Mannitol | − |
| Cellulose | − |
| Starch | + |
| Glycerol | + |
| Salicin | − |

Pridham-Gottlieb basal medium
*+, good utilization; −, poor or no utilization

This strain (AJ 9406) is as follows:
(1) Substrate mycelium
Not segmented
(2) Aerial mycelium
Simple branching, Retinaculi aperti, Spirales, and Rectiflexibles
Not formed on vegetative mycelium
Spore formation
Number of spores
(3) Special Breeding Organ such as Flagellated Spores and Globular Sporangia
Not detected
as shown in the morphological characteristics described above.

These results suggest that the strain AJ-9406 should be allocated to the genus Streptomyces.

From results of the above characteristics observed, properties of this microorganism (AJ-9406) are summarized as follows:
(1) Spore-bearing hyphae
Simple branching, Retinaculi aperti, Spirales, and Rectiflexibles
(2) Surface Structure of Spores
Smooth
(3) Color of aerial mycelium
Gray
(4) Color of substrate mycelium
Pale yellow brown→reddish
Reddish brown on starch-inorganic salts agar
(5) Distinctive color pigment
Not produced
(6) Sugar utilization
Sugar other than glucose and galactose: poor or not utilization
(7) Melanoid pigment formation
Negative According to the primary keys noted in Bargey's Manual, strain AJ-9406 belongs to the gray series of Streptomyces.

Comparing these microbiological characteristics with those of know species which was described in "The Actinomycetes (Vol II.)" written by S. A. Waksman and the "Cooperative description of Type Culture of Streptomyces II, III, IV, V" written by E. B. Shirling and D. Gottlieb (Int. J. Syst. Bact., 18, 69-189, 279-392, 19, 391-512, 22, 265-394) and the results were summarized in Table 3.

As shown in Table 3, microbiological characteristics of strain AJ-9406 were different from those of the known species. For example, Actinomyces cyanocolor, Streptomyces nogalater, St. griseoaurantiacus and St. viridifaciens produce the distinctive soluble pigment, while strain AJ-9406 does not product it. Moreover, the utilization pattern of carbon sources of these four species are different from that of strain AJ-9406.

St. recifensis, St. chibaensis and St. corchorusii do not produce the distinctive pigment in the substrate mycelium on starch-inorganic salts agar, while strain AJ-9406 produces it (reddish-brown). Moreover, the utilization pattern of carbon sources of those three species are different from that of strain AJ-9406.

St. carnosus produces the distinctive soluble pigment (pale pink or yellow) and utilizes rhamnose, while strain AJ-9406 neither produce the pigment nor utilize rhamnose.

TABLE 3

| Characteristics | Strain AJ-9406 | Actinomyces cyanocolar | Streptomyces nogalater | St. griseo-aurantiacus |
|---|---|---|---|---|
| Structure of[a] | RA, S, RF | S, RA, RF | S, RF, RA | S (RA) |

TABLE 3-continued

| | | | | |
|---|---|---|---|---|
| aerial mycelium | | | | |
| Surface structure of spore | Smooth | Smooth | Smooth | Smooth |
| Color of aerial mycelium | Gray | Gray OA[b] (Red) YM (Blue) GA, ISSA | Gray | Gray (Red) GA |
| Melanoic pigment | | | | |
| Peptone-yeast iron agar | − | − | − | − |
| Tyrosine agar | − | − | − | − |
| Tryptone-yeast liquid agar | − | − | − | − |
| Color of substrate mycelium | +[c] Reddish-brown (ISSA) | + Yellow, Yellow-brown | + Orange-yellow | + Orange-yellow Dark reddish-orange |
| Soluble pigment | − | + Violet | + Red, yellow | + Yellow-orange, Pinkish red |
| Utilization of carbon source | | | | |
| Glucose | +[d] | + | + | + |
| Arabinose | −[d] | + | + | + |
| Xylose | − | + | + | + |
| Inositol | − | + | − | +. |
| Mannitol | − | + | + | + |
| Fructose | − | +. | + | + |
| Rhamnose | − | + | + | + |
| Sucrose | − | − | − | − |
| Raffinose | − | − | +. | ± |
| Galactose | + | | | |

| | St. recifensis | St. chibaensis | St. carnosus | St. corchorusii | St. viridifaciens |
|---|---|---|---|---|---|
| | RA, RF Smooth Gray | S, RF Smooth Gray (Yellow) GA | RA, S Smooth Gray (Red) YM, OA | S, RF, RA Smooth Gray | RA, S, RF Smooth Gray |
| | − | − | − | − | − |
| | − | − | − | − | − |
| | − | − | − | − | − |
| | − | − | + Pale pink or yellow (OA, GA) | − | + Yellowish green |
| | + | + | + | + | + |
| | + | + | ± | + | + |
| | + | + | ± | + | + |
| | − | + | ± | + | − |
| | + | + | ± | + | + |
| | + | + | ± | + | + |
| | − | + | + | + | − |
| | + | + | ± | + | + |
| | + | + | − | + | − |

[a]RA: *Retinaculi-aperti,* S: Spirales, RF: Rectiflexibiles.
[b]ISSA: Inorganic salts-starch agar, OA: oatmeal agar, YM: Yeast-malt extract agar, GA: Glycerin-asparagine agar
[c]+ Produced distinctive color
− Not produced distinctive color
[d]+ Good utilization
± Doubtful or variable utilization
− Poor or no utilization From these results mentioned above, strain AJ-9406 should belong to the new species of the genus Streptomyces and was named *St. mozunensis.*

UTILITY IN INDUSTRY

Figure 1:
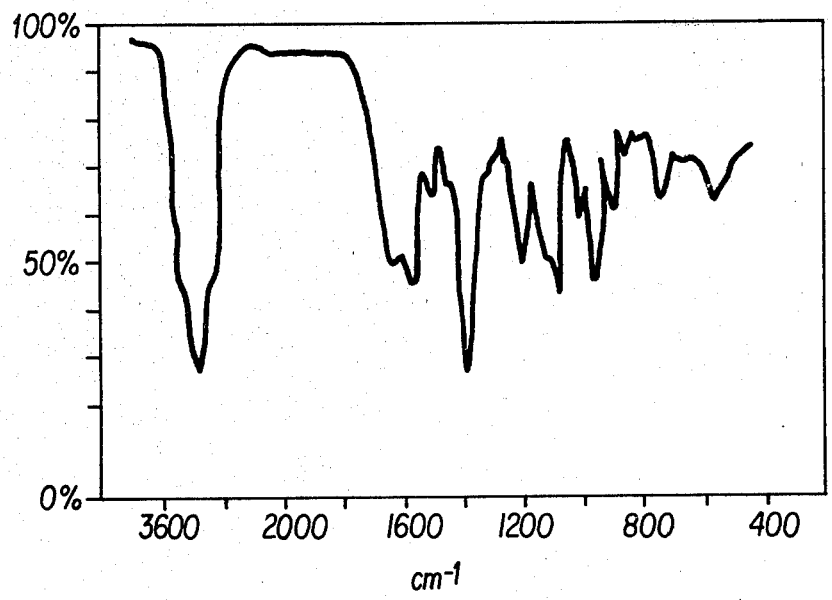
FIG. 1 shows an infrared spectrum of the novel tryptophan derivative (ammonium salt) in KBr Disk.
Axis of Ordinate: transmittance (%)
Axis Abscissa: wave number (cm$^{-1}$)

The novel tryptophan derivative has an inhibitory activity against a metallo proteinase, and therefore is useful for medicine such as an agent for treating *Pseudomonas aeruginosa* infectious disease and an agent for regulating growth of a microorganism.

We claim:
1. N-(6-Deoxy-L-talosyloxyhydroxyphosphinyl)-L-luecyl-L-tryptophan.

* * * * *